United States Patent [19]
Roorda et al.

[11] Patent Number: 5,972,369
[45] Date of Patent: Oct. 26, 1999

[54] DIFFUSIONAL IMPLANTABLE DELIVERY SYSTEM

[75] Inventors: Wouter E. Roorda, Newark, Calif.;
Keith E. Dionne, Cambridge, Mass.;
James E. Brown, Los Gatos, Calif.;
Jeremy C. Wright, Los Altos, Calif.;
Craig R. Davis, Newark, Calif.; Steven J. Prestrelski; Stelios T. Tzannis, both of Mountain View, Calif.

[73] Assignee: ALZA Corporation, Del.

[21] Appl. No.: 09/050,101

[22] Filed: Mar. 30, 1998

Related U.S. Application Data

[60] Provisional application No. 60/042,196, Mar. 31, 1997.

[51] Int. Cl.$^6$ .............................. A61F 2/02; A61K 9/22
[52] U.S. Cl. ..................... 424/424; 424/425; 604/892.1
[58] Field of Search ................................ 424/424, 425; 604/892.1

[56] References Cited

U.S. PATENT DOCUMENTS

| | | |
|---|---|---|
| Re. 34,365 | 8/1993 | Theeuwes . |
| 3,760,806 | 9/1973 | Leeper . |
| 3,760,984 | 9/1973 | Theeuwes . |
| 3,845,770 | 11/1974 | Theeuwes et al. . |
| 3,995,631 | 12/1976 | Higuchi et al. . |
| 4,135,514 | 1/1979 | Zaffaroni et al. . |
| 4,160,452 | 7/1979 | Theeuwes . |
| 4,217,894 | 8/1980 | Franetzki . |
| 4,468,220 | 8/1984 | Willbanks . |
| 4,720,384 | 1/1988 | Di Luccio et al. . |
| 4,838,862 | 6/1989 | Baker et al. . |
| 4,931,050 | 6/1990 | Idriss . |
| 4,994,273 | 2/1991 | Zetner et al. . |
| 5,041,107 | 8/1991 | Heil, Jr. . |
| 5,062,829 | 11/1991 | Pryor et al. . |
| 5,322,691 | 6/1994 | Darougar et al. . |
| 5,378,475 | 1/1995 | Smith et al. . |
| 5,466,233 | 11/1995 | Weiner et al. . |
| 5,516,522 | 5/1996 | Peyman et al. . |
| 5,728,396 | 3/1998 | Peery et al. ............................ 424/422 |

FOREIGN PATENT DOCUMENTS

| | | |
|---|---|---|
| 2046445 | 1/1992 | Canada . |
| 2721752 | 11/1978 | Germany . |
| 267665 | 5/1989 | Germany . |
| 2191701 | 12/1987 | United Kingdom . |
| WO91/00753 | 1/1991 | WIPO . |

OTHER PUBLICATIONS

Felix Franks, "Long–Term Stabilization of Biologicals", *Bio/Technology*, vol. 12, pp. 253–256, Mar. 12, 1994.

*Primary Examiner*—Carlos A. Azpuru
*Attorney, Agent, or Firm*—Burns, Doane, Swecker & Mathis, L.L.P.

[57] ABSTRACT

A sustained release delivery system for delivering a beneficial agent is provided. The system includes a reservoir comprising the beneficial agent and a capillary channel in communication with the reservoir and the exterior of the system for delivering the beneficial agent from the system. The capillary channel has a cross-sectional area and a length selected to deliver the beneficial agent at a predetermined rate. The system may further include an outer surface that is impermeable and non-porous during delivery of the beneficial agent. The beneficial agent may be formulated in a glassy sugar matrix.

31 Claims, 3 Drawing Sheets

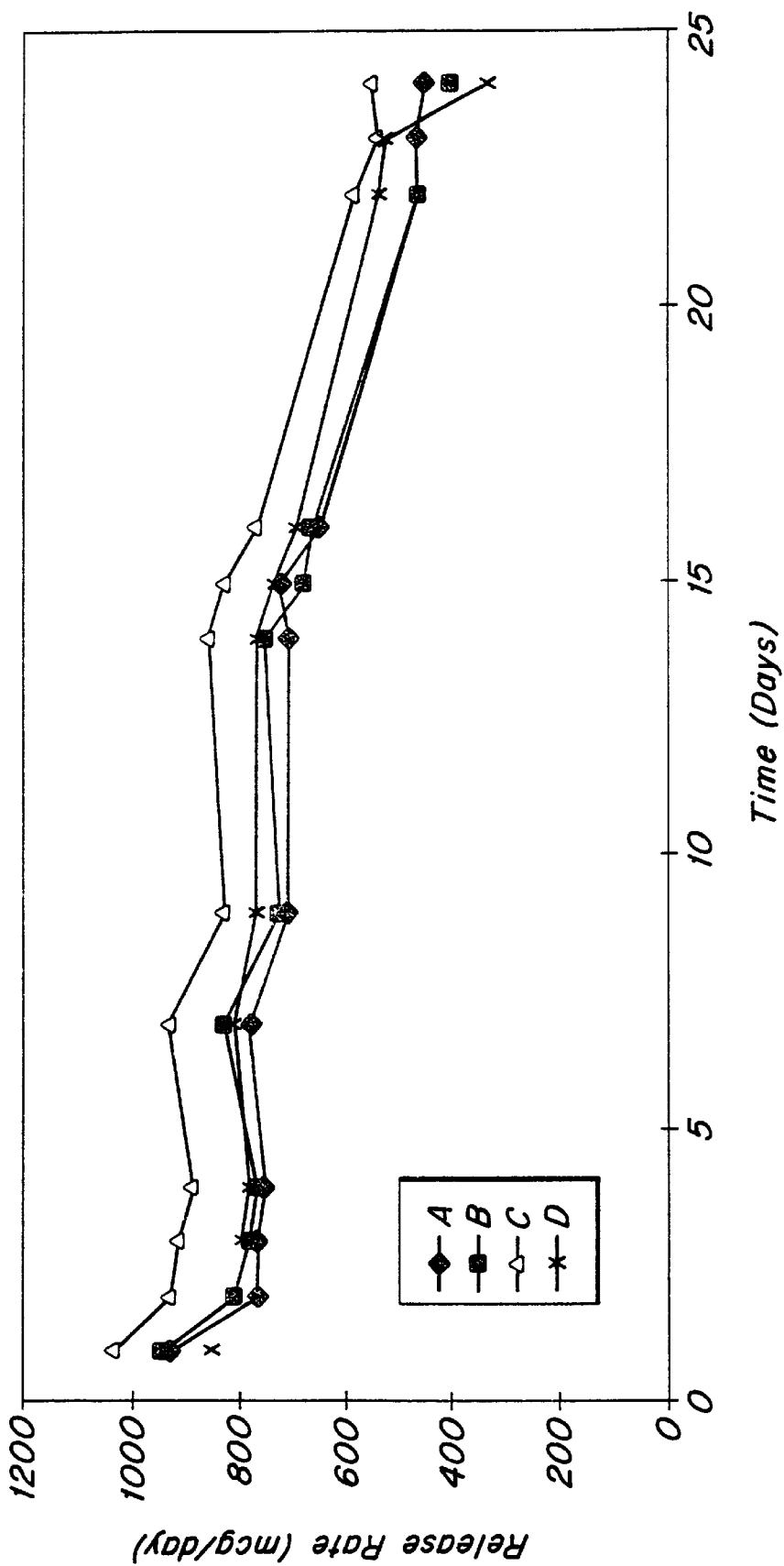

5,972,369

DIFFUSIONAL IMPLANTABLE DELIVERY SYSTEM

CROSS REFERENCE TO RELEVANT APPLICATION

This application claims the benefit of U.S. Provisional Application 60/042,196, filed on Mar. 31, 1997, pursuant to 35 U.S.C. §119(e).

BACKGROUND OF THE INVENTION

1. Field of the Invention

The present invention generally relates to a sustained release beneficial agent delivery system. More particularly, the invention relates to a sustained release beneficial agent delivery system having a capillary channel for controlling the rate of release of the beneficial agent by diffusion.

2. Description of the Related Art

Various dispensing systems for the delivery of active agents are known in the art. These systems generally deliver the active agent by diffusion from an enclosed capsule or from a multi-structured device having a wall formed of a polymer permeable to water and/or to the agent into a selected environment. See, e.g., U.S. Pat. Nos. 4,135,514; 3,760,806; 3,760,984; and 3,995,631. However, there is a large category of agents that cannot be readily delivered by such prior art systems because of at least one feature inherent in the devices which adversely affects the rate of release of the agent from the device. For example, many agents cannot be effectively delivered from a diffusion controlled delivery system because their permeation rate through the rate controlling material of the system is too small to produce a useful effect.

There is an additional class of active agents that also cannot be satisfactorily delivered by diffusional devices because of a particular chemical characteristic of the agent. This additional class includes salts that, because of their ionic character, will not readily diffuse through polymeric membranes. This class also includes unstable polar compounds that cannot be formulated into a satisfactory composition suitable for storage and delivery from such prior art systems.

In view of the above-mentioned disadvantages of prior art diffusional delivery systems and devices, there is a need in the art for a system that is capable of providing sustained delivery of beneficial agents, particularly, of beneficial agents that do not readily permeate through polymeric membranes.

SUMMARY OF THE INVENTION

It is, therefore, an object of the present invention to provide a diffusional delivery system suitable for the controlled and sustained release of a beneficial agent.

In one embodiment, the system includes a reservoir comprising a beneficial agent and a capillary channel in communication with the reservoir and the exterior of the device for delivering the beneficial agent from the device. The capillary channel has a cross-sectional area and a length selected to deliver the beneficial agent at a predetermined rate. The system further includes an outer surface that is impermeable and non-porous during delivery of the beneficial agent.

In another embodiment, the system includes a reservoir comprising a beneficial agent formulated in a glassy sugar matrix and a capillary channel in communication with the reservoir and the exterior of the device for delivering the beneficial agent from the device. The capillary channel has a cross-sectional area and a length selected to deliver the beneficial agent at a predetermined rate.

Another object of the present invention is to provide a method for delivering a beneficial agent at a predetermined rate using the sustained release delivery system according to the present invention. The method includes positioning the sustained release delivery system at a location in need of the beneficial agent or where release of the beneficial agent is desired, and allowing the beneficial agent to pass through the capillary channel of the delivery system to obtain a desired effect.

Another object of the present invention is to provide a method of preparing a sustained release delivery system for delivering a beneficial agent at a predetermined rate. The method includes the steps of providing a reservoir having an outer surface that is impermeable and non-porous during delivery of the beneficial agent, filling the reservoir with the beneficial agent, and providing the reservoir with a diffusion controller. The diffusion controller comprises a capillary channel having a cross-sectional area and a length selected to provide the predetermined rate.

Another object of the present invention is to provide a method of preparing a sustained release delivery system for delivering a beneficial agent formulated in a glassy sugar matrix at a predetermined rate. The method includes the steps of providing a reservoir, providing a beneficial agent formulated in a glassy sugar matrix in the reservoir, and providing the reservoir with a diffusion controller. The diffusion controller comprises a capillary channel having a cross-sectional area and a length selected to provide the predetermined rate.

Other objects, advantages, features, and aspects of the invention will become readily apparent in view of the following detailed description and the appended claims and drawings.

BRIEF DESCRIPTION OF THE DRAWINGS

The drawings, which are not drawn to scale, are provided to illustrate various embodiments of the invention. The drawings are as follows:

FIG. 4 is a graph showing the release rates as a function of time of the delivery systems prepared according to the example herein.

DESCRIPTION OF THE PREFERRED EMBODIMENTS

The present invention generally relates to a diffusional delivery system suitable for the controlled and sustained release of a beneficial agent.

In one preferred embodiment, the system includes a reservoir comprising a beneficial agent and a capillary channel in communication with the reservoir and the exterior of the system for delivering the beneficial agent from the system. The capillary channel has a cross-sectional area and a length selected to deliver the beneficial agent at a predetermined rate. The system further includes an outer surface that is impermeable and non-porous during delivery of the beneficial agent.

As used herein, the term "beneficial agent" refers to any composition or substance that will produce a pharmacological or physiological response in a mammalian organism. Such compositions and substances include drugs, medicaments, vitamins, nutrients, and the like. The term "beneficial agent" also refers to other compositions and substances that are delivered to other types of environments such as pools, tanks, reservoirs, and the like. Included among these types of compositions are biocides, sterilization agents, nutrients, vitamins, food supplements, sex sterilants, fertility inhibitors, and fertility promoters.

The term "impermeable" refers to a material that is sufficiently impermeable to environmental fluids as well as ingredients contained within the delivery system such that the migration of such fluids and ingredients into or out of the system through the impermeable material is so low as to have substantially no adverse impact on the function of the system.

The term "non-porous" refers to a material that is essentially free of holes, pores, or channels through which environmental fluids as well as ingredients contained within the delivery system could traverse during delivery of the beneficial agent.

In addition, as used herein, the term "capillary channel" refers to a generally narrow, elongated passage through which ingredients inside the reservoir may move outside of the delivery system and environmental fluids outside the system may move inside to the reservoir. As will be explained hereinbelow, the capillary channel has a length and cross-sectional area selected to delivery the beneficial agent from the system at a desired rate by diffusion.

Figure 1:
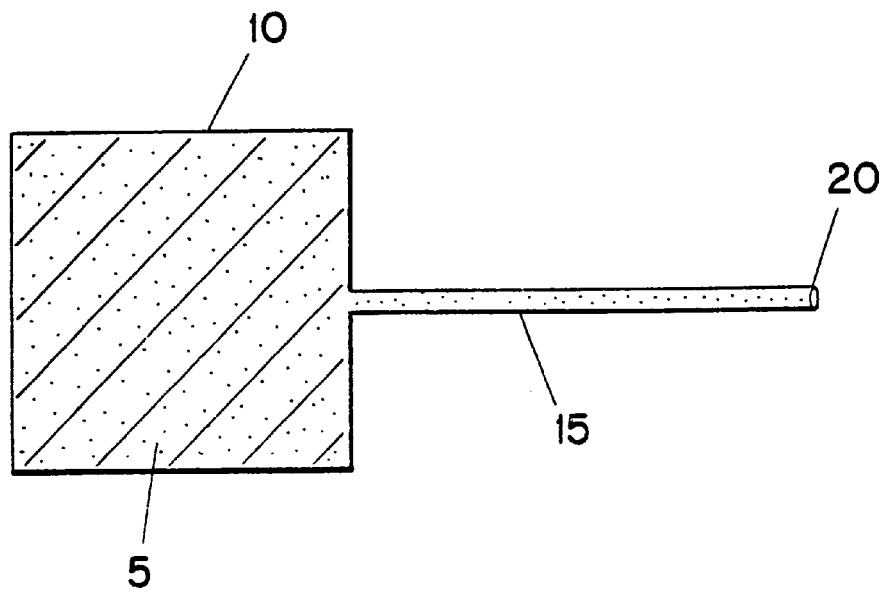
FIG. 1 is an enlarged view of one embodiment of the sustained release beneficial agent delivery system showing a beneficial agent reservoir and a long, narrow capillary channel.

FIG. 1 illustrates one embodiment of the sustained release beneficial agent delivery system of the present invention. While the system shown in FIG. 1 is generally cylindrical, the system can be in any shape. The system comprises a reservoir 5 containing a beneficial agent, an outer surface 10 that is impermeable and non-porous, and a capillary channel 15 having a cross-sectional area and a length selected to deliver the beneficial agent from reservoir 5 to an area outside of the system at a predetermined rate. Capillary channel 15 contains an orifice 20 through which the beneficial agent inside reservoir 5 exits the system as well as through which environmental fluid outside of the system may enter reservoir 5.

Figure 2:
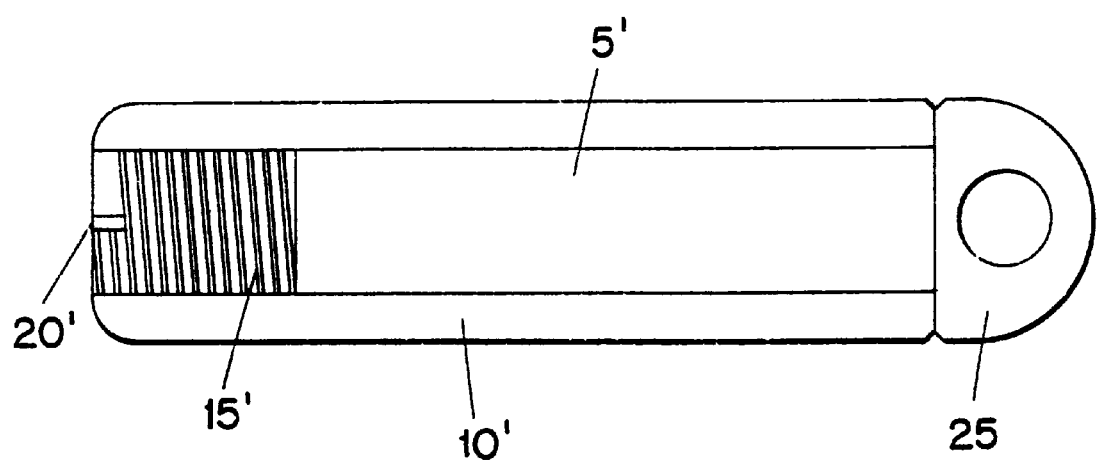
FIG. 2 is an enlarged view of another embodiment of the sustained release beneficial agent delivery system showing a beneficial agent reservoir, a long, narrow capillary channel, and an implant attachment.

FIG. 2 illustrates another embodiment of the sustained release beneficial agent delivery system of the present invention. Again, while the system shown in FIG. 2 is generally cylindrical, the system can be in any shape. The system similarly comprises a reservoir 5' containing a beneficial agent, an outer surface 10' that is impermeable and non-porous, and a capillary channel 15' having a cross-sectional area and a length selected to deliver the beneficial agent from reservoir 5' to an area outside of the system at a predetermined rate. Here, the capillary channel 15' has a helical configuration. FIG. 2 further shows an orifice 20' in communication with capillary channel 15' through which the beneficial agent inside reservoir 5' exists the system as well as through which environmental fluid outside of the system may enter reservoir 5'. FIG. 2 also shows an attachment 25 for affixing the system when it is implanted into a mammalian subject. Attachment 25 is shown here in the form of a ring. However, attachment 25 may be of any shape known in the art for affixing a sustained release delivery system in an environment of use, e.g., for affixing an implant inside a mammalian body or for affixing a device in a tank or other environment of use.

The system according to the present invention has particular applicability in providing a controlled and sustained release of beneficial agents effective in obtaining a desired local or systemic physiological or pharmacological effect relating at least to the following areas: treatment of cancerous primary tumors (e.g., glioblastoma); chronic pain; arthritis; rheumatic conditions; hormonal deficiencies such as diabetes and dwarfism; and modification of the immune response such as in the prevention of transplant rejection and in cancer therapy. A wide variety of other disease states are known by those of ordinary skill in the art, such as those described in Goodman and Gilman, *The Pharmacological Basis of Therapeutics*, 8th ed., Pergamon Press, NY, 1990; and *Remington's Pharmaceutical Sciences*, 18th ed., Mack Publ. Co., Easton, Pa., 1990; both of which are hereby incorporated by reference.

In addition to the above, the system is suitable for use in treating mammalian organisms infected with AIDS and AIDS related opportunistic infections such as cytomegalovirus infections, toxoplasmosis, pneumocystis carinii and mycobacterium avium intercellular. For example, the system may be used to delivery a beneficial agent effective in treating fungal infection in the mouth of AIDS patients. If such a use is desired, the system may be designed to have a shape suitable for implanting into a tooth of the patient.

The system is particularly useful for treating ocular conditions such as glaucoma, proliferative vitreoretimopathy, diabetic retinopathy, uveitis, and keratitis. The system is also particularly useful as an ocular system in treating mammalian organisms suffering from cytomegalovirus retinitis wherein the system is surgically implanted within the vitreous of the eye.

Suitable classes of beneficial agents for use in the system of the present invention include, but are not limited to the following:

1. Peptides and proteins such as cyclosporin, insulin, growth hormones, insulin related growth factor, heat shock proteins and related compounds;
2. Anesthetics and pain killing agents such as lidocaine and related compounds, and benzodiazepam and related compounds;
3. Anti-cancer agents such as 5-fluorouracil, adriamycin and related compounds;
4. Anti-inflammatory agents such as 6-mannose phosphate;
5. Anti-fungal agents such as fluconazole and related compounds;
6. Anti-viral agents such as trisodium phosphomonoformate, trifluorothymidine, acyclovir, cidofovir, ganciclovir, DDI and AZT;
7. Cell transport/mobility impending agents such as colchicine, vincristine, cytochalasin B and related compounds;
8. Anti-glaucoma drugs such as beta-blockers: timolol, betaxolol atenolol, etc.;
9. Immunological response modifiers such as muramyl dipeptide and related compounds;

10. Steroidal compounds such as dexamethasone, prednisolone and related compounds; and 11. Carbonic anhydrase inhibitors.

In addition to the above agents, other beneficial agents which are suitable for administration, especially to the eye and its surrounding tissues, to produce a local or a systemic physiologic or pharmacologic effect can be used in the system of the present invention. Examples of such agents include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antivirials such as idoxuridine; and other antibacterial agents such as nitrofurazone and sodium propionate; antiallergenics such as antazoline, methapyriline, chlorpheniramine, pyrilamine, and prophenpyridamine; anti-inflarnmatories such as hydrocortisone, hydrocortisone acetate, dexamethasone 21-phosphate, fluocinolone, medrysone, methylprednisolone, prednisolone 21-phosphate, prednisolone acetate, fluorometalone, betamethasone, and triminolone; decongestants such as phenylephrine, naphazoline, and tetrahydrazoline; miotics and anti-cholinesterases such as pilocarpine, esterine salicylate, carbachol, diisopropyl fluorophosphate, phospholine iodine, and demecarium bromide; mydriatics such as atropine sulfate, cyclopentolate, homatropine, scopolamine, tropicamide, eucatropine, and hydroxyamphetamine; and sympathomimetics such as epinephrine.

Any pharmaceutically acceptable form of the aforementioned beneficial agents may be employed in the practice of the present invention, e.g., the free base or a pharmaceutically acceptable salt or ester thereof. Pharmaceutically acceptable salts, for instance, include sulfate, lactate, acetate, stearate, hydrochloride, tartrate, maleate and the like. Beneficial agents which are water soluble are particularly useful in the present invention.

The beneficial agents may also be used in combination with pharmaceutically acceptable carriers and, optionally, additional ingredients such as antioxidants, stabilizing agents, diffusion enhancers, and the like. For example, where water uptake by the beneficial agent is undesired, the beneficial agent can be formulated in a hydrophobic carrier, such as a wax or an oil, that would allow sufficient diffusion of the beneficial agent from the system.

In a preferred embodiment, the beneficial agents, e.g., proteins, may be formulated in a glassy matrix of sugar which tends to protect the beneficial agent from hydrolytic degradation.

A large number of materials can be used to construct the system of the present invention. The only requirements are that they are suitably inert and are impermeable and non-porous as defined hereinabove. When the system according to the present invention is used in the body, the material selected should also be biocompatible. Materials that are suitable for fabricating the present invention include naturally occurring or synthetic materials, especially those, that are biologically compatible with body fluids and eye tissues, and essentially insoluble over an extended period of time in the fluids with which the material will come into contact. The use of rapidly dissolving materials, materials that are highly soluble in eye fluids, or materials that develop pores, holes, or channels during delivery of the beneficial agent are to be avoided since dissolution or break down of the outer surface of the system would affect the constancy of the controlled release of the beneficial agent as well as the capability of the system to remain in place for a prolonged period of time.

Naturally occurring or synthetic materials that are biologically compatible with body fluids and eye tissues suitable for use in the present invention generally include metals, ceramics, glass, polymers, and combinations thereof. Examples of such polymeric materials include polyethylene, polypropylene, polyethylene terephthalate, plasticized polyvinyl chloride, crosslinked polyester, polycarbonate, polysulfone, polystyrene, poly(2-pentene), poly(methylmethacrylate), poly(1,4-phenylene), polytetrafluoroethylene, and poly-ethylene-vinylacetate (EVA). Preferred polymers include polyethylene and polypropylene. Preferred polymers may be chosen according to their biocompatibility, degree of impermeability, transparency to light, or ability to be detected by external measurement such as ultrasound or x-ray.

Preferably, the polymer is also bioerodible. Suitable bioerodible polymers include poly(glycolic acid), poly(lactic acid), copolymers of lactic/glycolic acid, polyorthoesters, polyanhydrides, polyphosphazones, and polycaprolactone. These polymers are particularly preferred because of their slow erosion properties and should not undergo undue changes during the course of the beneficial agent delivery.

Exemplary metals suitable for use in the present invention include titanium, stainless steel, tin, and aluminum. Preferably, the metal is titanium or a titanium alloy.

The outer surface of the system as well as the capillary channel may be made of any of the above-listed materials or combinations thereof. The outer surface and the capillary channel can be constructed of the same or different material. For example, the outer surface material of the system can be a metal while the material defining the capillary channel can be a polymer.

The system according to the present invention may be made in a variety of ways. For example, if the system is going to be made entirely of a polymer, then the polymer can be injection molded or die cast into a desired shape and size. An effective amount of the beneficial agent is then obtained, for example, in an aqueous solution formulation. The beneficial agent can be filled into the reservoir and into the capillary channel by any conventional means such as a syringe or a pipette. Care should be taken in filling the system with the beneficial agent so as to avoid any air pockets in the reservoir or the capillary channel because the air pocket could act as a lock, preventing wetting and/or migration of the beneficial agent to the desired location outside of the system. Thus, in this embodiment, at the very least, the capillary channel should be filled with a medium that draws water into the reservoir. This medium could be water itself, an aqueous solution of the beneficial agent, or any biocompatible water attracting agent initially present as a solid.

The above description of how to make the system of the present invention is merely illustrative and should not be considered as limiting the scope of the invention in any way, as various methods for making the system would be readily apparent to one skilled in the art. In particular, the methods of making the system depend on the identity of the beneficial agent as well as the outer surface material. Given the beneficial agent and material selected, one skilled in the art could easily make the system of the present invention using conventional fabrication techniques.

Naturally, the system according to the present invention can be manufactured to hold any quantity of the beneficial agent desired. The cross-sectional area and the length of the capillary channel can also be varied to obtain the desired rate of delivery as more fully explained below.

The system according to the present invention is a diffusional beneficial agent delivery system in which control over the diffusion of the beneficial agent is exerted by the capillary channel.

Mathematically, a diffusional process can be described by Fick's Law:

$$J = -D \cdot A \cdot (\Delta C / l)$$

in which J is the mass transport of the beneficial agent from the system, D is the diffusivity of the beneficial agent, A is the surface area through which the diffusion takes place, $\Delta C$ is the concentration difference of the beneficial agent inside and outside of the delivery system, and l is the length of the diffusional path.

In prior art systems, the primary method for controlling the mass transport J of a beneficial agent from a reservoir containing the agent is to surround the reservoir with a membrane through which the beneficial agent has a relatively low diffusivity D. Adjustments in the surface area A and thickness l of the membrane can then be made to obtain the desired mass transport.

In direct contrast to the prior art systems, it is particularly preferred that the system according to the present invention does not contain a permeable or semipermeable membrane through which the beneficial agent or environmental fluid must pass in order for the beneficial agent to be delivered. Thus, in the present invention, the rate of delivery of the beneficial agent is not controlled by the beneficial agent's diffusivity through the material surrounding the reservoir. Instead, it is controlled by selecting the surface area A (i.e., the cross-sectional area of the capillary channel) and the diffusional path length l (i.e., the length of the capillary channel) through which the diffusion takes place. The smaller the value of A and the larger the value of l, the lower the mass transport will be.

For any desired rate of delivery, the particular cross-sectional area A and length l of the capillary channel can be determined based on Fick's Law above. It is within the level of one skilled in the art to determine the cross-sectional area A and length l of the capillary channel once the diffusivity D of the beneficial agent, the mass transport J, and the difference in concentration $\Delta C$ of the beneficial agent from inside to outside of the system are known. Generally, the diffusivity D of a particular beneficial agent (e.g., drugs) through a particular medium can be calculated experimentally or by consulting standard handbooks or review articles known to those skilled in the art. See, e.g., *Remington's*, pp. 1680–81; and R. W. Baker & H. K. Lonsdale, Controlled Release: Mechanisms and Rates in ADVANCES IN EXPERIMENTAL MEDICINE AND BIOLOGY, Vol. 47, pp. 15–71 (Tanqaury & Lacey eds., 1974), the contents of which are incorporated by reference.

The mass transport J, in the case where the beneficial agent is a drug, is selected based on the effective dosage of the drug. Typical dosages of drugs for particular ailments may be found in standard medical handbooks. See, e.g., Goodman & Gilman; *Physician's Desk Reference* (PDR); and *The Extra Pharmacopeia* (Royal Pharm. Soc.), the contents of which are incorporated by reference. The difference in concentration $\Delta C$ can been determined easily based on the concentration of the beneficial agent inside the reservoir of the system, which is usually known, and the concentration of the same beneficial agent outside the system, which is typically about zero, but may be greater than zero depending on the specific beneficial agent. Once the values of J, D, and $\Delta C$ have been ascertained, then Fick's Law may be used to determine acceptable values for A and l which would then define the cross-sectional area and length required for the capillary channel.

As is readily apparent, the method of mass transport control according to the present invention is fundamentally different from the use of a permeable membrane. One important advantage in using such a method to control the mass transport is that the system of the present invention can be used to deliver hydrophilic molecules, which are notoriously difficult to deliver from a membrane controlled diffusional system.

It is also important to note that the method of delivery of the present invention is not the same as restricting the flow of a liquid by using a narrow orifice. In fact, preferably, there is no viscous flow of liquid through the capillary channel of the system. In this preferred embodiment, the capillary channel is filled with a loosely crosslinked, highly swollen, but immobilized gel through which diffusion of the beneficial agent can take place. Such gels include swollen polyacrylates, polymethacrylates, crosslinked gelatins, crosslinked carbohydrates such as NaCMC, HPMC and HPC, alginates, aluminum stearate gels, and PVP gels.

Another advantage of the system according to the present invention is that there are no moving parts and, thus, it would be easier to fabricate than plunger-type osmotic delivery systems known in the art.

As noted above, the system according to the present invention could be employed to treat a mammalian organism to obtain a desired local or systemic physiological or pharmacological effect. The system could be employed by administering the sustained release beneficial agent delivery system to the mammalian organism and allowing the beneficial agent therein to pass out of the system to come in direct contact with the mammalian organism.

The beneficial agent delivery system of the present invention may be administered to a mammalian organism via any route of administration known in the art. Such routes of administration include intraocular, oral, subcutaneous, intramuscular, intraperitoneal, intranasal, dermal, intrathecal, and the like. In addition, one or more of the systems may be administered at one time or more than one agent may be included in the reservoir or inner core.

The beneficial agent delivery system of the present invention is particularly suitable for direct implantation into the vitreous humor of the eye and for application to an intraocular lens.

These methods of administration and techniques for their preparation are well known by those of ordinary skill in the art. Techniques for their preparation are set forth, for example, in *Remington's Pharmaceutical Sciences*.

The beneficial agent delivery system may be administered at a suitable location for a sufficient period of time and under conditions which allow treatment of the disease state of concern.

For localized beneficial agent delivery, the system of the present invention may be surgically implanted at or near the site of action. This is the case when it is used in treating ocular conditions, primary tumors, rheumatic and arthritic conditions, and chronic pain.

For systemic relief, the system may be implanted subcutaneously, intramuscularly or intraperitoneally. This is the case when the system is to give sustained systemic levels and avoid premature metabolism.

In one particularly preferred embodiment of the invention, an intra-ocular implant system containing cidofovir as the beneficial agent in an effective amount to treat AIDS induced cytomegalovirus retinitis infection of the eye may be prepared. It has been estimated that cidofovir would be effective in treating this disease at dosages of 0.5 to 2 $\mu$g/day when delivered directly into the vitreous humor.

Cidofovir has three ionizable sites and, thus, is not expected to diffuse readily through polymeric membranes. It is highly soluble (>150 mg/ml) in water and is extremely stable in aqueous solution. Thus, it is very suitable for use in the system according to the present invention.

In this embodiment, the reservoir of the system and the capillary channel would be filled with a saturated aqueous solution of cidofovir. Assuming that the diffusivity D of cidofovir in water is $1\times10^{-6}$ cm$^2$/s and its solubility $\Delta C$ in water is 150 mg/ml, then a desired dosage of 1 $\mu$g/day can be obtained with a capillary channel having a length of 1 cm and a diameter of 0.1 mm. If the reservoir is initially filled with at least about 730 $\mu g$ of cidofovir, then the system could deliver cidofovir for two years or longer. Such a system may remain in the vitreous humor permanently after treatment is complete.

Generally, the amount of beneficial agent used in the system of the present invention ranges from about 0.01 mg to about 2.5 g. Preferably, the system contains from about 1 mg to about 100 mg of the beneficial agent. Most preferably, the system contains from about 1 mg to about 10 mg of the beneficial agent. These preferred ranges may provide sustained release of the beneficial agent for a period of from several days to over one year.

Preferably, the capillary channel of the system according to the present invention has a substantially circular cross-sectional area. In which case, the capillary channel preferably has a diameter of about 0.01 mm to about 1 mm, and a length of about 0.1 cm to about 25 cm. The system as a whole preferably has a diameter of about 0.1 mm to about 10 mm, and a length of about 1 mm to about 50 mm. When such a system is prepared for implantation within the vitreous of the eye, it is preferred that the system does not exceed about 5 mm in any direction. Thus, the cylindrical system shown in FIGS. 1 and 2 would preferably not exceed 5 mm in length or diameter.

In a separate preferred embodiment, the system according to the present invention includes a reservoir comprising a beneficial agent formulated in a glassy sugar matrix and a capillary channel communicating between the reservoir and the exterior of the system for delivering the beneficial agent from the system. The capillary channel has a cross-sectional area and a length selected to deliver the beneficial agent at a predetermined rate.

Here, there is no requirement that the outer surface of the system be impermeable and non-porous during delivery of the beneficial agent as in the first embodiment described above. However, it is contemplated by the present invention that the outer surface of the system in this embodiment could be impermeable and non-porous during delivery of the beneficial agent.

Preferably, the beneficial agent employed in this system is a peptide or protein such as those mentioned hereinabove.

It has recently been suggested that beneficial agents, particularly proteins, formulated in glass matrices may extend their shelf life and eliminate the need for cold storage. See, e.g., F. Franks, Long-Term Stabilization of Biologicals, BIO/TECHNOLOGY, Vol. 12, pp. 253–56 (March 1994); the contents of which are hereby incorporated by reference.

Proteins may be formulated in a glass matrix by removing water from a homogeneous solution thereof. The water can be removed either by evaporation or by rapidly cold quenching the solution. This process is commonly referred to as vitrification. As water is removed from the solution, it becomes increasingly viscous until a "solidified" liquid containing the proteins is obtained. The "solidified" liquid is generically called glass.

Glasses have a number of unique physical and chemical properties which make them ideal for beneficial agent formulation. Among them, the most important is that the solidified liquid retains the molecular disorder of the original solution. This disorder contributes to the glasses' long-term stability by preventing crystallization and chemical reactions of the proteins encased therein.

Sugars can also play an important part in stabilizing protein formulations. In solution, they are known to shift the denaturation equilibrium of proteins toward the native state. Most sugars, particularly low molecular weight carbohydrates, are also known to vitrify easily and to provide a glassy matrix that retards inactivating reactions of the proteins.

For illustrative purposes, the glassy sugar matrix for use in the system according to the present invention can be made by compressing a lyophilized mix of a protein with a sugar and a buffer, and optionally, binders. The protein-sugar matrix should be incorporated into the system with minimal inclusion of air. Various ways are known in the art for such incorporation. Preferably, upon vitrification, the formulation chosen will have a glass transition temperature ($T_g$) above the environmental temperature. The $T_g$ of a formulation is a function of the relative amounts of the formulation components, and its determination is known to those skilled in the art.

Alternatively, the protein may be vitrified or encased in the glassy sugar matrix directly in the reservoir of the delivery system.

Examples of proteins and proteinaceous compounds which may be formulated and employed in the delivery system according to the present invention include those proteins which have biological activity or which may be used to treat a disease or other pathological condition. They include, but are not limited to growth hormone, Factor VIII, Factor IX and other coagulation factors, chymotrypsin, trysinogen, alpha-interferon, beta-galactosidase, lactate dehydrogenase, growth factors, clotting factors, enzymes, immune response stimulators, cytokines, lymphokines, interferons, immunoglobulins, retroviruses, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and goserelin, LHRH agonists and antagonists, growth hormone releasing factor, calcitonin, colchicine, gonadotropins such as chorionic gonadotropin, oxytocin, octreotide, somatotropin plus an amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagon, endocrine agents secreted internally and distributed by way of the bloodstream, and the like. Other agents which may be encased and delivered include $\alpha_1$ antitrypsin, insulin and other peptide hormones, adrenal cortical stimulating hormone, thyroid stimulating hormone, and other pituitary hormones, interferon $\alpha$, $\beta$ and $\delta$, erythropoietin, growth factors such as GCSF, GM-CSF, insulin-like growth factor 1, tissue plasminogen activator, CF4, dDAVP, tumor necrosis factor receptor, pancreatic enzymes, lactase, interleukin-1receptor antagonist, interleukin-2, tumor suppresser proteins, cytotoxic proteins, viruses, viral proteins, recombinant antibodies and antibody fragments and the like. Analogs, derivatives, antagonists, agonists, and pharmaceutically acceptable salts of the above may also be used.

The above agents are useful for the treatment or prevention of a variety of conditions including, but not limited to hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointesinal and other cancers.

The protein compounds useful in the formulations of the present invention can be used in the form of a salt, preferably a pharmaceutically acceptable salt. Useful salts are known to those skilled in the art and include salts with inorganic acids, organic acids, inorganic bases, or organic bases.

Sugars useful for preparing the glassy matrix include, but are not limited to glucose, sucrose, trehalose, lactose, maltose, raffinose, stachyose, maltodextrins, cyclodextrins, sugar polymers such as dextrans and their derivatives, ficoll, and starch.

Buffers useful for formulating the glassy matrix include, but are not limited to MES, HEPES, citrate, lactate, acetate, and amino acid buffers.

Preferably, the system comprising the glassy sugar matrix is constructed of a bioerodible polymer with a low water permeability. Such polymers include poly(glycolic acid), poly(lactic acid), copolymers of lactic/glycolic acid, polyorthoesters, polyanhydrides, polyphosphazones, polycaprolactone. These polymers are particularly preferred because of their slow erosion properties and low water uptake; thus, they should not undergo undue changes during the course of the beneficial agent delivery.

In operation, the osmotically active glassy sugar protein matrix may absorb some water through the polymer material. However, with the proper selection of polymer material, water uptake through the polymer wall can be minimized. Thus, the capillary channel would be the predominant route of mass transport as well as the primary method for controlling the rate of delivery of the protein. Specifically, the rate at which the glassy sugar protein matrix dissolves is determined primarily by the rate of water uptake through the capillary channel and the rate of release of the sugar. As in the first embodiment, the rate of protein released from the system in this embodiment is determined by its diffusion through the capillary channel. Again, for a given concentration of protein, this rate can be adjusted by changing the length and the cross-sectional area of the capillary channel.

Simply put, the dimensions of the capillary channel control the amount of water that is drawn into the reservoir and, thus, control the rate at which the sugar matrix dissolves. At the same time, the dimensions of the capillary channel control the rate of delivery of the protein from the system.

An advantage of this embodiment of the invention is that as long as the protein is inside the delivery system, it is protected either by the glassy sugar matrix or by the presence of the dissolved stabilizer molecules that once formed the sugar matrix. Thus, by using the system according to the present invention, it is possible to obtain a sustained and controlled release of a protein that retains more biological activity than conventional formulations.

The system according to this embodiment of the invention can be made and used in the same manner as the system of the first embodiment described above.

The following example is merely illustrative of the present invention and should not be considered as limiting the scope of the invention, as the example and other equivalents thereof will become more apparent to those skilled in the art in light of the present disclosure.

EXAMPLE

Figure 3:
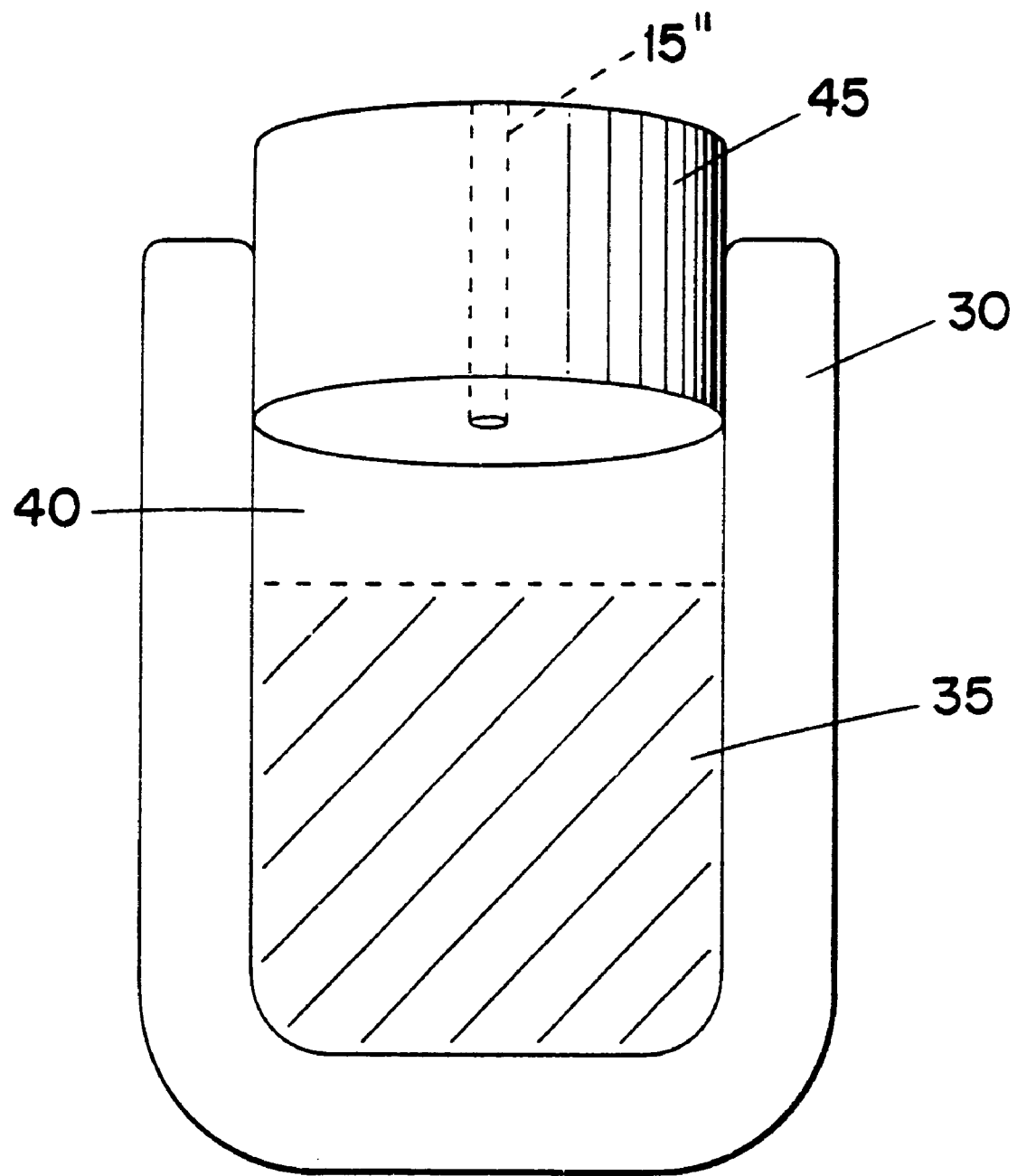
FIG. 3 is an enlarged view of the sustained release delivery system prepared according to the example herein.

Four cylindrical cups, labeled A, B, C, and D, were provided as the reservoir. The cups were made of acrylate, and had a length of 2 cm, an outside diameter of 8 mm, and an inside diameter of 4 mm. The cups were left open at one end for filling with the beneficial agent. An enlarged view of the delivery system of this Example can be seen in FIG. 3.

A slurry of bupivacaine hydrochloride in a saturated aqueous solution thereof was provided as the beneficial agent. The cups 30 were all filled with enough of the slurry such that, after settling, they all contained a layer of solid drug 35 of about 1 cm thick and a layer of saturated solution of drug 40 on top of the solid layer. No attempt was made to quantify the amount of drug in the cups in any other way.

A diffusion controller 45 containing a capillary channel 15" was then inserted into the open end of each of the cups. The diffusion controller 45 was made of acrylate and had a cylindrical shape. The diffusion controller 45 had a length of 5 mm and a diameter of about 4 mm. A 1 mm orifice was drilled into each of the diffusion controllers in the axial direction to provide the capillary channel 15".

Great care had to be taken to remove air from the cups because initial experiments were repeatedly hampered by small air bubbles blocking the capillary channel in the diffusion controller. It is believed that the best way to remove the small air bubbles is to fill the cups with a de-aerated slurry of the drug, and then draw a vacuum on the cups several times before capping them with the diffusion controllers.

Each of the cups 30 was then glued in a vertical position to the bottom of a scintillation vial. The vials were filled with 15 ml of water, which was replaced at regular intervals and measured for drug content. The vials were shaken at 37° C. in a Dubnoff type water bath. The experiment was continued until most of the cups no longer contained visible amounts of solid drug.

The release rates of each of the delivery systems A, B, C, and D are graphically shown in FIG. 4 as a function of time. As seen in FIG. 4, each of the delivery systems released the drug at a relatively constant and reproducible rate. In particular, although the systems show a slight burst of drug release at day 1, from day 2 through day 23 the delivery rates were relatively constant. At day 24, the effects of drug depletion became evident in system D. The average release rates of the four systems range from 835 mcg/day at day 2 to 530 mcg/day at day 23.

The results of this example demonstrate that it is possible to achieve relatively constant release rates over a substantial period of time by using a diffusional delivery system according to the present invention.

While the invention has been described and illustrated with reference to certain preferred embodiments thereof, those skilled in the art will appreciate that various modifications, changes, omissions, and substitutions can be made without departing from the spirit and scope of the invention. As such, these changes and/or modifications are properly and equitably intended to be within the full range of equivalence of the following claims.

We claim:

1. A sustained release diffusional delivery system comprising:
   a beneficial agent;
   a reservoir that encloses said beneficial agent, an entirety of said reservoir that encloses said beneficial agent being impermeable and non-porous to fluids external of said reservoir during delivery of the beneficial agent; and a capillary channel in communication with said reservoir and the exterior of the system for delivering said beneficial agent from the system;

said capillary channel having a cross-sectional area and a length selected to provide a predetermined delivery rate of said beneficial agent.

2. The system according to claim 1, wherein said beneficial agent is cidofovir.

3. The system according to claim 1, wherein said beneficial agent is a protein or peptide.

4. The system according to claim 3, wherein said protein is occluded in a glassy sugar matrix.

5. The system according to claim 1, wherein said capillary channel is filled with said beneficial agent.

6. The system according to claim 1, wherein said capillary channel is filled with an immobilized gel capable of diffusing said beneficial agent from said reservoir to the exterior of the system.

7. The system according to claim 1, wherein said capillary channel is filled with water.

8. The system according to claim 1, wherein said outer surface is selected from the group consisting of metals, ceramics, glass, and polymers.

9. The system according to claim 8, wherein said outer surface is a bioerodible polymer.

10. The system according to claim 9, wherein said bioerodible polymer is selected from the group consisting of poly(glycolic acid), poly(lactic acid), copolymers of lactic/glycolic acid, polyorthoesters, polyanhydrides, polyphosphazones, and polycaprolactones.

11. The system according to claim 8, wherein said non-porous material is titanium or a titanium alloy.

12. The system according to claim 1, wherein said capillary channel is helical.

13. The system according to claim 1, wherein said system is capable of being implanted into a mammalian organism.

14. The system according to claim 13, further comprising a ring at one end thereof for affixing said system inside said mammalian organism.

15. The system according to claim 1, wherein said system is capable of continuously delivering from about 0.5 to about 2 µg/day of said beneficial agent.

16. The system according to claim 1, wherein said system is capable of continuously delivering said beneficial agent over a period of at least two years.

17. The system according to claim 1, wherein said capillary channel has a diameter of about 0.01 mm to about 1 mm.

18. The system according to claim 1, wherein said capillary channel has a length of about 0.1 cm to about 25 cm.

19. The system according to claim 1, having a cylindrical shape.

20. The system according to claim 19, having a diameter of about 0.1 mm to about 10 mm, and a length of about 1 mm to about 50 mm.

21. A sustained release delivery system for delivering a beneficial agent formulated in a glassy sugar matrix at a predetermined rate, comprising:

(a) a reservoir comprising said beneficial agent formulated in a glassy sugar matrix; and (b) a capillary channel in communication with said reservoir and the exterior of the system for delivering said beneficial agent from the system, said capillary channel having a cross-sectional area and a length selected to provide said predetermined rate.

22. The system according to claim 21, wherein said beneficial agent is a protein or peptide.

23. The system according to claim 22, wherein said system is made of a bioerodible polymer.

24. The system according to claim 23, wherein said bioerodible polymer is selected from the group consisting of poly(glycolic acid), poly(lactic acid), copolymers of lactic/glycolic acid, polyorthoesters, polyanhydrides, polyphosphazones, and polycaprolactones.

25. A method of delivering a beneficial agent at a predetermined rate, said method comprising positioning a sustained release diffusional delivery system at a location in need of such beneficial agent, said sustained release diffusional delivery system comprising:

(a) a reservoir that encloses said beneficial agent, an entirety of said reservoir that encloses said beneficial agent being impermeable and non-porous to fluids external of said reservoir during delivery of the beneficial agent; and (b) a capillary channel in communication with said reservoir and the exterior of the system for delivering said beneficial agent from the system;

said capillary channel having a cross-sectional area and a length selected to provide said predetermined rate.

26. A method of delivering a beneficial agent formulated in a glassy sugar matrix at a predetermined rate, said method comprising positioning a sustained release delivery system at a location in need of the beneficial agent formulated in a glassy sugar matrix, said sustained release delivery system comprising:

(a) a reservoir comprising said beneficial agent; and (b) a capillary channel in communication with said reservoir and the exterior of the system for delivering said beneficial agent from the system, said capillary channel having a cross-sectional area and a length selected to provide said predetermined rate.

27. A method of preparing a sustained release delivery system for delivering a beneficial agent at a predetermined rate, said method comprising the steps of:

(a) providing a reservoir that encloses the beneficial agent, an entirety of said reservoir that encloses said beneficial agent being impermeable and non-porous to fluids external of said reservoir during delivery of the beneficial agent;

(b) filling said reservoir with the beneficial agent; and (c) providing the reservoir with a diffusion controller, said diffusion controller comprising a capillary channel having a cross-sectional area and a length selected to provide said predetermined rate.

28. A method of preparing a sustained release delivery system for delivering a beneficial agent formulated in a glassy sugar matrix at a predetermined rate, said method comprising the steps of:

(a) providing a reservoir;

(b) providing a beneficial agent formulated in a glassy sugar matrix in said reservoir; and (c) providing the reservoir with a diffusion controller, said diffusion controller comprising a capillary channel having a cross-sectional area and a length selected to provide said predetermined rate.

29. The system according to claim 21, wherein said reservoir encloses said beneficial agent, an entirety of said reservoir that encloses said beneficial agent being impermeable and non-porous to fluids external of said reservoir during delivery of said beneficial agent.

30. The method of delivering a beneficial agent according to claim 26, wherein said reservoir encloses said beneficial agent, an entirety of said reservoir that encloses said beneficial agent being impermeable and non-porous to fluids external of said reservoir during delivery of said beneficial agent.

31. The method of delivering a beneficial agent according to claim 28, wherein said reservoir encloses said beneficial agent, an entirety of said reservoir that encloses said beneficial agent being impermeable and non-porous to fluids external of said reservoir during delivery of the beneficial agent.

* * * * *